US00PP33203P2

(12) United States Plant Patent
Ranney et al.

(10) Patent No.: US PP33,203 P2
(45) Date of Patent: Jun. 29, 2021

(54) ***VIBURNUM* PLANT NAMED 'NCVX3'**

(50) Latin Name: ***Viburnum davidii* x *propinquum***
Varietal Denomination: NCVX3

(71) Applicant: North Carolina State University, Raleigh, NC (US)

(72) Inventors: Thomas Green Ranney, Arden, NC (US); Darren Touchell, Raleigh, NC (US); Irene Palmer, Raleigh, NC (US); Andra Nus, Raleigh, NC (US); Nathan P. Lynch, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

(21) Appl. No.: 16/903,218

(22) Filed: Jun. 16, 2020

(51) Int. Cl.
*A01H 5/02* (2018.01)
*A01H 6/00* (2018.01)

(52) U.S. Cl.
USPC ..... Plt./226
CPC ..... *A01H 6/00* (2018.05)

(58) Field of Classification Search
USPC ..... Plt./226, 263.1
CPC ..... A01H 5/00; A01H 5/02; A01H 5/12
See application file for complete search history.

(56) References Cited

PUBLICATIONS https://plantoftheweek.com/2020/05/28/plant-of-the-week-yin-and-yang-viburnum/; May 28, 2020; 3 pages.*
https://www.provenwinners.com/plants/viburnum/yang-david-viburnum-viburnum; Oct. 14, 2020; 3 pages.*

* cited by examiner

*Primary Examiner* — Kent L Bell
(74) *Attorney, Agent, or Firm* — Cassandra Bright

(57) ABSTRACT

A new and distinct cultivar of *Viburnum* plant named 'NCVX3' is disclosed, characterized by a unique compact, prostrate habit and glossy, dark evergreen leaves. The new variety is a *Viburnum*, normally produced as an outdoor garden or container plant.

3 Drawing Sheets

Latin name of the genus and species: *Viburnum davidii* x *propinquum.*

Variety denomination: 'NCVX3'.

BACKGROUND OF THE INVENTION

The new *Viburnum* cultivar is a product of a planned breeding program conducted by the inventor in Mills River, N.C. The cross resulting in this new variety was made during Summer of 2010. The objective of the breeding program was to develop new plant forms of *Viburnum* for commercial horticultural purposes.

The seed parent of 'NCVX3' is the unpatented, proprietary seedling referred to as 'NCSU 2007-187'. The pollen parent is the unpatented, proprietary seedling referred to as 'NCSU 2007-080'. The new variety was identified as a potentially interesting selection in the July of 2012, at a research greenhouse in Mills River, N.C.

The first asexual propagation of 'NCVX3' was carried out in July of 2012 by rooting stem cuttings at the same research greenhouse in Mills River, N.C. and has been asexually reproduced repeatedly. 'NCVX3' has been found to retain its distinctive characteristics through successive asexual propagations.

SUMMARY OF THE INVENTION

The cultivar 'NCVX3' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'NCVX3'. These characteristics in combination distinguish 'NCVX3' as a new and distinct *Viburnum* cultivar:

1. A compact, prostrate habit.
2. Glossy, dark evergreen leaves.
3. Abundant white flowers in spring.

PARENT COMPARISON

Plants of the new cultivar 'NCVX3' are similar to plants of the seed parent in most horticultural characteristics, however, plants of the new cultivar 'NCVX3' differ in the following;

1. The new variety has lighter green foliage.
2. The new variety has smaller flowers than the seed parent.

Plants of the new cultivar 'NCVX3' are similar to plants of the pollen parent in most horticultural characteristics, however, plants of the new cultivar 'NCVX3' differ in the following;

1. Plants of 'NCVX3' are more compact than plants of the pollen parent.
2. Flowers of the new variety are larger and showier than the flowers of the pollen parent.

COMMERCIAL COMPARISON

Plants of the new cultivar 'NCVX3' can be compared to the commercial variety *Viburnum* 'Jermyns Globe', unpatented. These varieties are similar in most horticultural characteristics; however, 'NCVX3' differs in the following:

1. The new variety produces lighter green foliage, this comparator produces darker green foliage with a blue tinge.
2. Flower buds of 'NCVX3' are white, flower buds of this comparator are pink.

'NCVX3' can also be compared to 'NCVX2', U.S. Plant patent application Ser. No. 16/903,184. 'NCVX3' is smaller in size (height: 50 to 70 cm; width: 90 to 120 cm), with a more prostrate habit, smaller leaves (length 2.2 to 6 cm; width: 1 to 2.5 cm), and a larger inflorescence diameter (5 to 10 cm.). Compared to 'NCVX3', 'NCVX2' is larger in size (height: 80 to 120 cm; width: 100 to 120 cm), with a globose habit, larger leaves (length 4 to 9 cm; width: 1.5 to 3.7 cm), and a smaller inflorescence diameter (4 to 5 cm).

BRIEF DESCRIPTION OF THE PHOTOGRAPHS

This new smooth-leaf *Viburnum* (*Viburnum davidii* x *propinquum*) is illustrated by the accompanying photographs which show the plant's form, foliage and inflorescences. The colors shown are as true as can be reasonably obtained by conventional photographic procedures. Colors in the photographs may differ slightly from the color values cited in the detailed botanical description, which accurately describe the colors of the new *Viburnum* cultivar. Age of the plant is about 2 years.

DETAILED BOTANICAL DESCRIPTION

Figure 1:
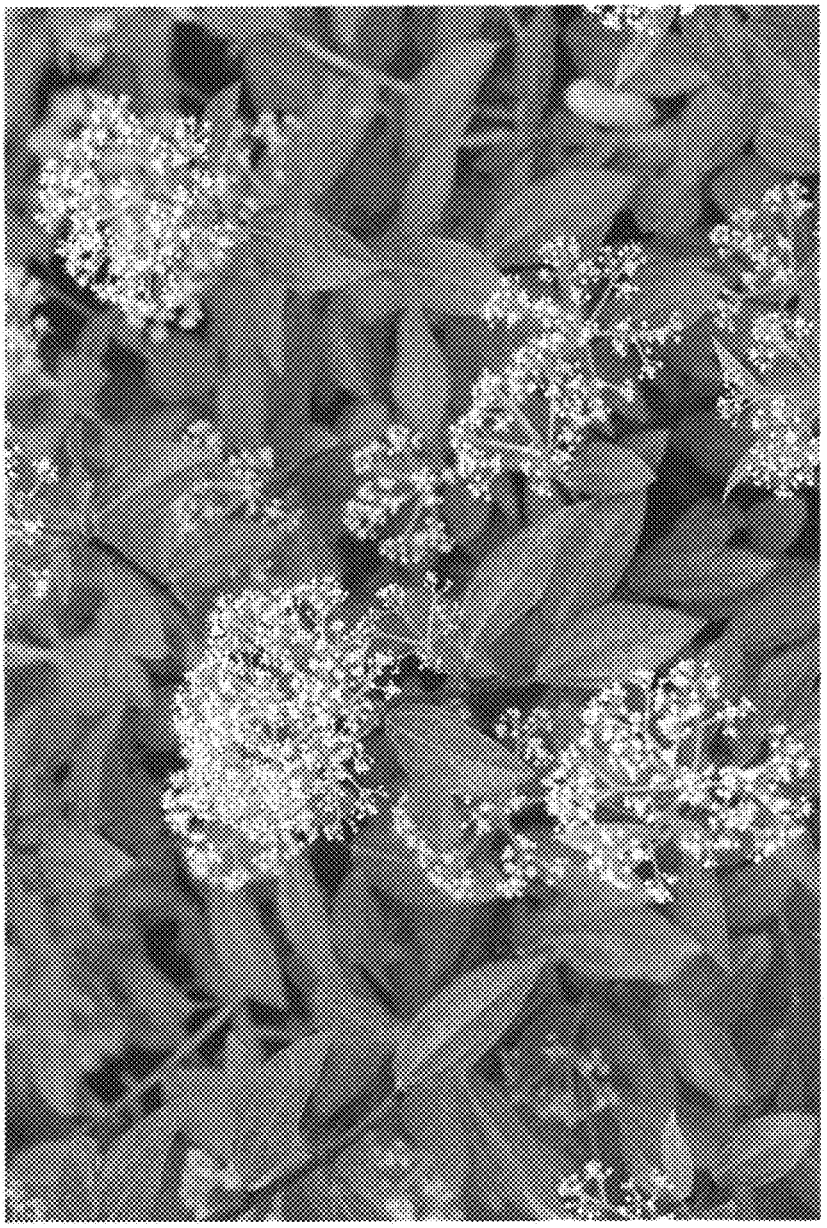
FIG. 1 is a photograph showing white inflorescences and dark green foliage of 'NCVX3' taken in Grand Haven, Mich. in May 2019.
Figure 2:
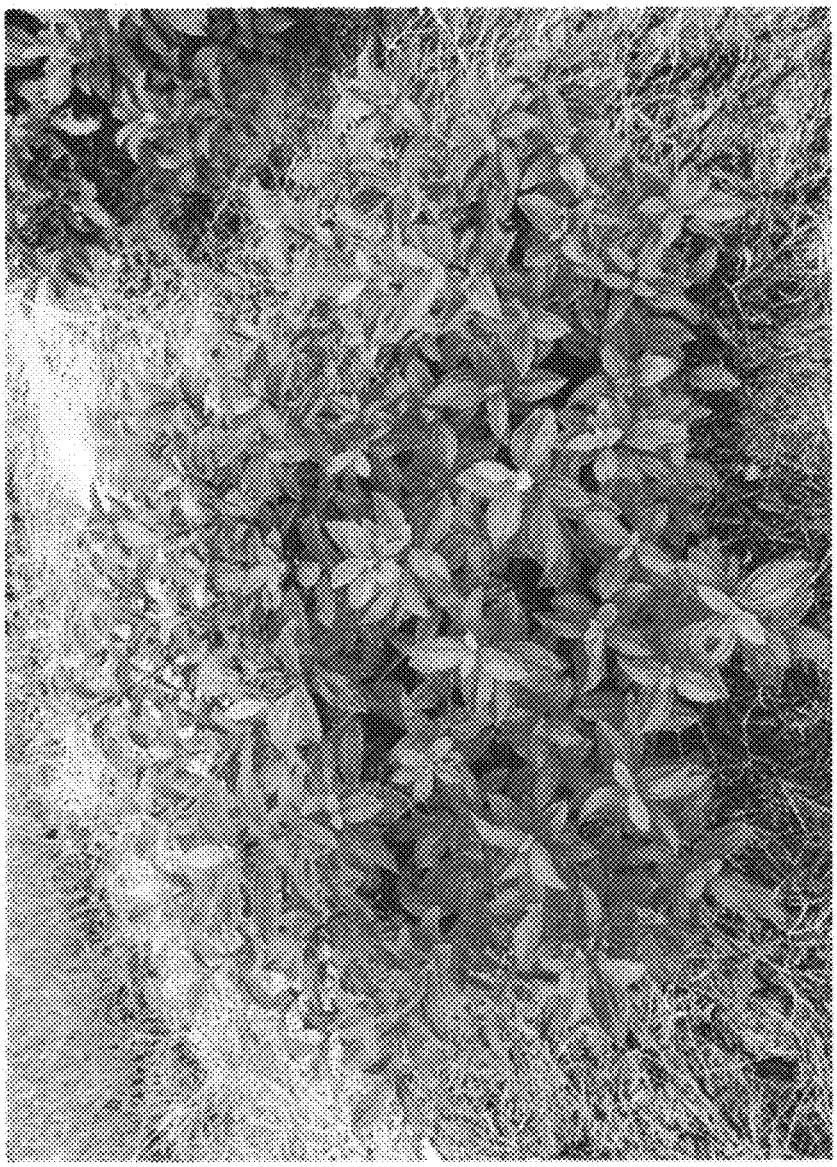
FIG. 2 is a photograph showing the habit of a field-grown plant of 'NCVX3' taken in Jackson Springs N.C. in September 2019.
Figure 3:
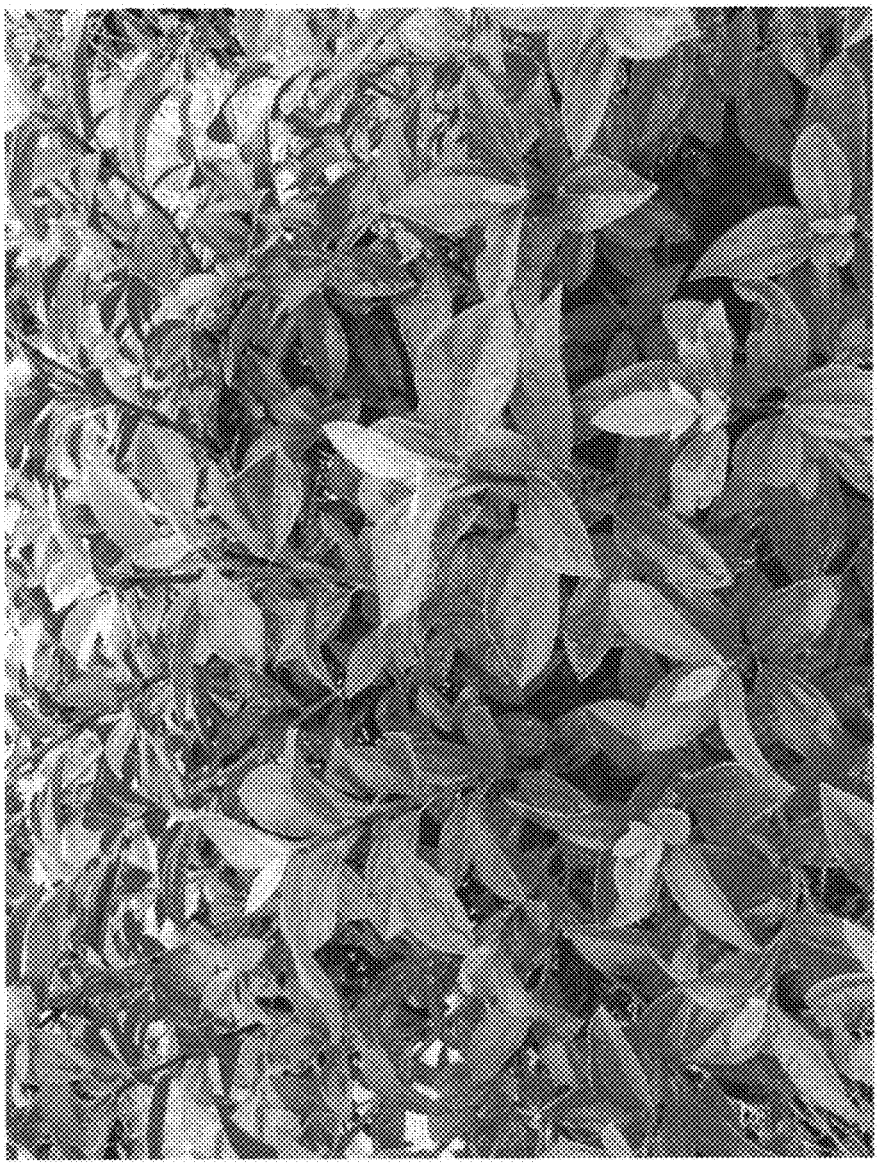
FIG. 3 is a photograph of the dark green lustrous foliage of 'NCVX3' taken in Jackson Springs N.C. in September 2019.

The following is a detailed description of the botanical characteristics of the new and distinct smooth *Viburnum* (*Viburnum davidii* x *propinquum*) known by the denomination 'NCVX3'. The detailed description was taken on a 3-year-old field-grown plant in Jackson Springs, N.C. in 2019. All colors cited herein refer to The Royal Horticultural Society Colour Chart (The Royal Horticultural Society (R.H.S.), London, 2001 Edition). Where pertinent, descriptive data was supplemented with information provided from cooperators in Grand Haven, Mich. where data was taken on 3-year-old container plants as well as plants in a landscape setting. Where specific dimensions, sizes, colors, and other characteristics are given, it is to be understood that such characteristics are approximations or averages set forth as accurately as practicable.

Botanical classification: *Viburnum davidii* x *propinquum* 'NCVX3'.

PROPAGATION

Typical method: Softwood cuttings.

Time to initiate rooting: 28 days at approximately 27° C.

Time to produce a rooted young plant: About 3 months at approximately 27° C.

Root description: Dense, free branching roots of moderate thickness. Colored yellow-white, not accurately measured with an R.H.S. chart.

PLANT

Plant type: Perennial evergreen flowering shrub.

Plant description:

*Growth habit.*—Densely branched, prostrate.

*Height.*—50 to 70 cm.

*Width.*—90 to 120 cm.

Shoot and stem:

*Lateral branch length.*—Avg. 24 cm (18 to 30 cm).

*Lateral branch diameter.*—Avg. 0.4 cm (0.2 to 0.5 cm).

*Internode length.*—Avg. 4.5 cm (1 to 7 cm).

*Immature shoot texture* (*current year*).—Glabrous.

*Immature shoot color* (*current year*).—Greyed-Purple (187A).

*Mature stem texture* (*from prior year*).—Glabrous, with lenticels and fissures.

*Mature stem color* (*from prior year*).—Brown (200C).

Plant vigor: Moderate.

FOLIAGE

Leaf:

Type: Simple.

*Persistence.*—Evergreen.

*Arrangement.*—Opposite.

*Shape.*—Elliptical.

*Apex.*—Acute.

*Base.*—Rounded.

*Venation.*—Pinnate.

*Vein color.*—Upper: Red-Purple (59A). Lower: Greyed-Purple (184C).

*Margins.*—Entire or obscurely denticulate.

*Emerging leaves.*—Color: Upper: Greyed-Purple (183A). Lower: Green (138B). Texture: Glabrous.

*Mature leaves during growing season.*—Color: Upper: Green (NN137A). Lower: Yellow-Green (147B). Texture: Coriaceous and glabrous. Length of lamina: Avg. 4 cm (2.2 to 6 cm). Width: Avg. 2 cm (1 to 2.5 cm).

*Leaf attachment.*—Petiolate.

*Petiole.*—Length: Avg. 0.8 cm (0.6 to 1 cm). Diameter: 0.1 cm Color: Purple (N77A). Texture: Glabrous.

Flower:

*Description.*—Single flowers arranged on terminal cymes.

*Flower longevity.*—About 1 week.

*Number of flowers per inflorescence.*—50 to 250.

*Flowering season.*—Mid-April to early May in Mills River, N.C.

*Fragrance.*—Slight fragrance.

*Inflorescence.*—Diameter: Average 8 cm (5 to 10 cm). Height: Average 4 cm (2 to 6.5 cm).

*Flower.*—Diameter: 0.5 cm. Height: 0.4 cm.

*Bud.*—Shape: Round. Length: About 0.2 cm. Diameter: About 0.2 cm. Color: White (155B).

*Petals.*—Number: 5 fused, reflexed petals. Arrangement: Whorled. Length: 0.2 cm. Width: 0.1 cm. Shape: Oblong. Margin: Entire. Apex: Rounded. Texture: Glabrous. Color: White (155D).

*Sepal.*—Number: 5. Arrangement: Whorled. Length: Less than 0.1 cm. Width: Less than 0.1 cm. Shape:

Fused. Margin: Entire. Apex: Acute. Base: Fused. Texture: Glabrous. Color: Green (143C).

*Peduncle*.—Length: Average 4.5 cm (3 to 6 cm). Diameter: About 0.2 cm. Texture: Glabrous. Color: Yellow-Green (144C).

*Pedicels*.—Length: Average 0.4 cm (0.1 to 0.6). Diameter: Less than 0.1 cm. Texture: Glabrous. Color: Yellow-Green (144B).

REPRODUCTIVE ORGANS

Gynoecium:

*Pistil number*.—1.

*Pistil length*.—Less than 0.1 cm.

*Stigma shape*.—Rounded.

*Stigma color*.—Yellow-Green (144D).

*Style length*.—Less than 0.1 cm.

*Style color*.—Yellow-Green (144D).

Androecium:

*Stamen number*.—5.

*Anther shape*.—Oblong.

*Anther size*.—Less than 0.1 cm.

*Anther color*.—Brown (200A).

*Amount of pollen*.—Moderate.

*Pollen color*.—White (155B).

OTHER CHARACTERISTICS

Fruit and seed: None observed.

Disease and insect resistance: No significant resistance nor susceptibility to disease or insect pests has been observed.

Cold hardiness: At least USDA zone 7a; testing has not been completed in colder zones.

What is claimed is:

1. A new and distinct cultivar of *Viburnum* plant named 'NCVX3' as herein illustrated and described.

* * * * *